US00PP28516P3

(12) United States Plant Patent
Oates et al.

(10) Patent No.: US PP28,516 P3
(45) Date of Patent: Oct. 10, 2017

(54) ***AEONIUM* PLANT NAMED 'MOBAMAGNUM'**

(50) Latin Name: *Aeonium arboreum*
Varietal Denomination: MOBamagnum

(71) Applicants: John David Oates, Millingandi (AU); Malcolm Morgan, Picton (AU)

(72) Inventors: John David Oates, Millingandi (AU); Malcolm Morgan, Picton (AU)

( * ) Notice: Subject to any disclaimer, the term of this patent is extended or adjusted under 35 U.S.C. 154(b) by 110 days.

(21) Appl. No.: 14/757,051

(22) Filed: Nov. 11, 2015

(65) Prior Publication Data

US 2017/0135273 P1 May 11, 2017

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Aeonium* plant named 'MOBamagnum', characterized by its upright and compact plant habit; moderately vigorous to vigorous growth habit; freely basal branching habit; green and dark purple-colored leaves; and good keeping quality and garden performance.

2 Drawing Sheets

Botanical designation: *Aeonium arboreum.*
Cultivar demonination: 'MOBamagnum'.

BACKGROUND OF THE INVENTION

The present invention relates to a new and distinct *Aeonium* plant, botanically known as *Aeonium arboreum* and hereinafter referred to by the cultivar name 'MOBamagnum'.

The new *Aeonium* plant is a product of a planned breeding program conducted by the Inventors in Tura Beach and Picton, New South Wales, Australia. The objective of the breeding program is to create new compact *Aeonium* plants with good basal branching habit and short internodes.

The new *Aeonium* plant originated from a cross-pollination made by the Inventors in Tura Beach, New South Wales, Australia in September, 2008, of a proprietary selection of *Aeonium arboreum* identified as code number 272, not patented, as the female, or seed parent with a proprietary selection of *Aeonium arboreum* identified as code number 1678, not patented, as the male, or pollen, parent. The new *Aeonium* plant was discovered and selected by the Inventors as a single plant from within the progeny of the stated cross-pollination in a controlled environment in Picton, New South Wales, Australia in August, 2010.

Asexual reproduction of the new *Aeonium* plant by vegetative cuttings in Picton, New South Wales, Australia since February, 2011 has shown that the unique features of this new *Aeonium* plant are stable and reproduced true to type in successive generations.

SUMMARY OF THE INVENTION

Plants of the new *Aeonium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MOBamagnum'. These characteristics in combination distinguish 'MOBamagnum' as a new and distinct *Aeonium* plant:

1. Upright and compact plant habit.
2. Moderately vigorous to vigorous growth habit.
3. Freely basal branching habit.
4. Green and dark purple-colored leaves.
5. Good keeping quality and garden performance.

Plants of the new *Aeonium* differ primarily from plants of the female and male parent selections in plant habit as plants of the new *Aeonium* are more compact than plants of the female and male parent selections. Additionally, plants of the new *Aeonium* have a freely basal branching habit whereas plants of the female and male parent selections do not have a freely basal branching habit.

Plants of the new *Aeonium* can be compared to plants of the *Aeonium arboreum* 'Velour', not patented. In side-by-side comparisons conducted in Picton, New South Wales, Australia, plants of the new *Aeonium* differed primarily from plants of 'Velour' in the following characteristics:

1. Plants of the new *Aeonium* were more compact than plants of 'Velour'.
2. Plants of the new *Aeonium* were more freely basal branching than plants of 'Velour'.
3. Leaves of plants of the new *Aeonium* were narrower than leaves of plant of 'Velour'.
4. Plants of the new *Aeonium* and 'Velour' differed in leaf color as plants of 'Velour' had green-colored leaves with red-colored margins.

BRIEF DESCRIPTION OF THE PHOTOGRAPHS

The accompanying photographs illustrate the overall appearance of the new *Aeonium* plant showing the colors as true as it is reasonably possible to obtain in colored reproductions of this type. Colors in the photographs may differ slightly from the color values cited in the detailed botanical description which accurately describe the colors of the new *Aeonium* plant.

The photograph on the first sheet is a side perspective view of typical plants of 'MOBamagnum'.

The photograph on the second sheet is a close-up view of typical plants of 'MOBamagnum'.

DETAILED BOTANICAL DESCRIPTION

The aforementioned photographs and following observations and measurements describe plants grown during the winter in 20-cm containers in an outdoor nursery under full sunlight conditions in Picton, New South Wales, Australia and under cultural practices typical of commercial *Aeonium* plant production. During the production of the plants, day temperatures ranged from 18° C. to 40° C. and night temperatures ranged from −2° C. to 10° C. Plants were one year old when the photographs and description were taken. In the following description, color references are made to The Royal Horticultural Society Colour Chart, 2001 Edition, except where general terms of ordinary dictionary significance are used.

Botanical classification: *Aeonium arboreum* 'MOBamagnum'.

Parentage:

*Female, or seed, parent*.—Proprietary selection of *Aeonium arboreum* identified as code number 272, not patented.

*Male, or pollen, parent*.—Proprietary selection of *Aeonium arboreum* identified as code number 1678, not patented.

Propagation:

*Type*.—By vegetative cuttings.

*Time to initiate roots, summer*.—About twelve days at temperatures about 21° C.

*Time to initiate roots, winter*.—About three weeks at temperatures about 25° C.

*Time to produce a rooted young plant, summer*.—About four weeks at temperatures about 21° C.

*Time to produce a rooted young plant, winter*.—About two months at temperatures about 18° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; medium density to dense.

Plant description:

*Plant and growth habit*.—Upright and compact plant habit; moderately vigorous to vigorous growth habit; moderate to fast growth rate.

*Plant height*.—About 45 cm.

*Plant diameter or spread*.—About 60 cm.

*Branching habit*.—Freely basal branching habit with numerous basal branches developing per plant.

*Branch length*.—About 20 cm.

*Branch diameter*.—About 1.25 cm.

*Internode length*.—About 5 mm.

*Strength*.—Strong.

*Aspect*.—Semi-erect to horizontal.

*Texture*.—Smooth, glabrous.

*Luster*.—Semi-glossy; with development, matte.

*Color, developing*.—Close to 146D.

*Color, fully developed*.—Close to 199B.

Leaf description:

*Arrangement*.—In basal rosettes.

*Length*.—About 5 cm.

*Width*.—About 1.5 cm.

*Shape*.—Roughly spatulate.

*Apex*.—Acuminate.

*Base*.—Cuneate.

*Margin*.—Ciliate.

*Texture, upper and lower surfaces*.—Smooth, glabrous.

*Luster, upper surface*.—Matte to semi-glossy.

*Luster, lower surface*.—Matte.

*Venation pattern*.—Parallel.

*Color*.—Developing leaves, upper surface: Close to 146B; towards the margins, close to 59B. Developing leaves, lower surface: Close to 147B to 147C; towards the margins, close to 59B. Fully expanded leaves, upper surface: Close to N187A. Fully expanded leaves, lower surface: Close to N186C. Venation, upper and lower surfaces: Similar to surface coloration.

Flower description: Flower initiation and development has not been observed on plants of the new *Aeonium*.

Disease & pest tolerance: Plants of the new *Aeonium* have not been shown to be tolerant to *Botrytis* and Mildew pathogens. Plants of the new *Aeonium* have not been observed to tolerant to pests common to *Aeonium* plants.

Keeping quality: Good keeping quality; plants of the new *Aeonium* are durable and to have good keeping quality for about 45 days.

Garden performance: Plants of the new *Aeonium* have been observed to have good garden performance and to tolerate wind, rain, full sunlight and temperatures ranging from about −2° C. to about 40° C.

It is claimed:

1. A new and distinct *Aeonium* plant named 'MOBamagnum' as illustrated and described.

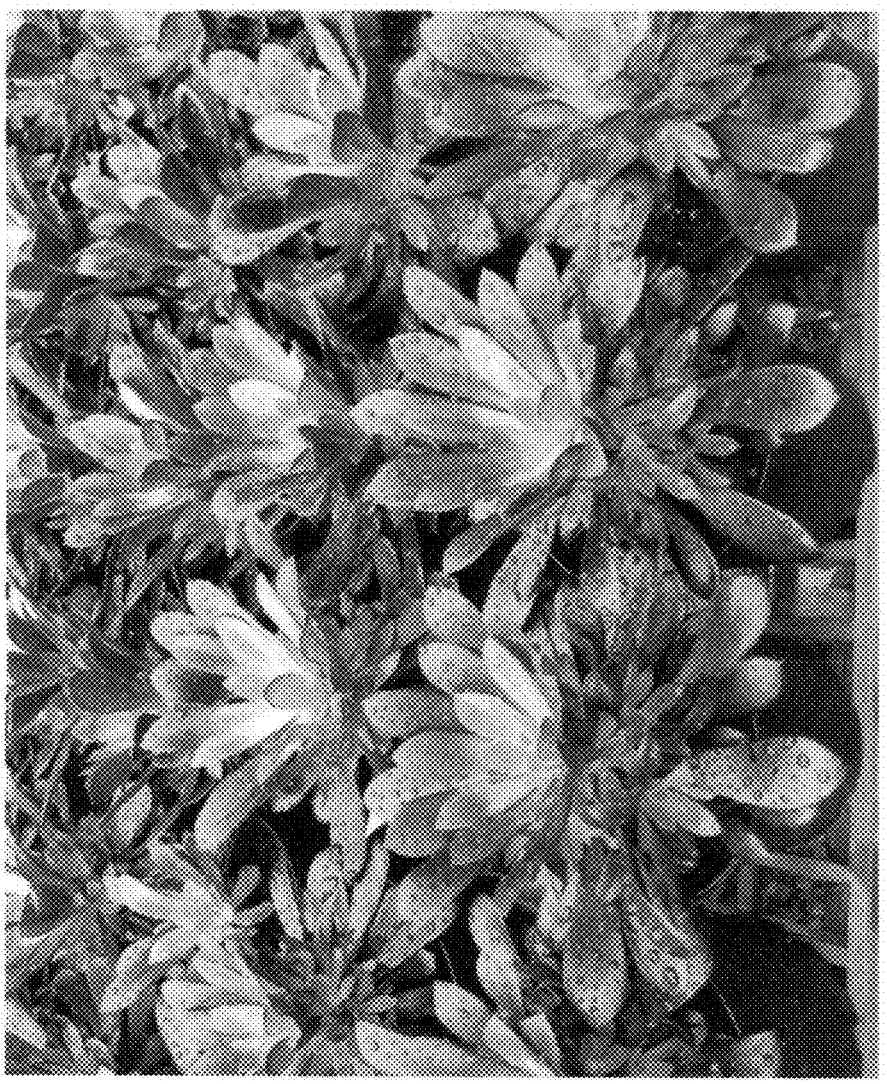

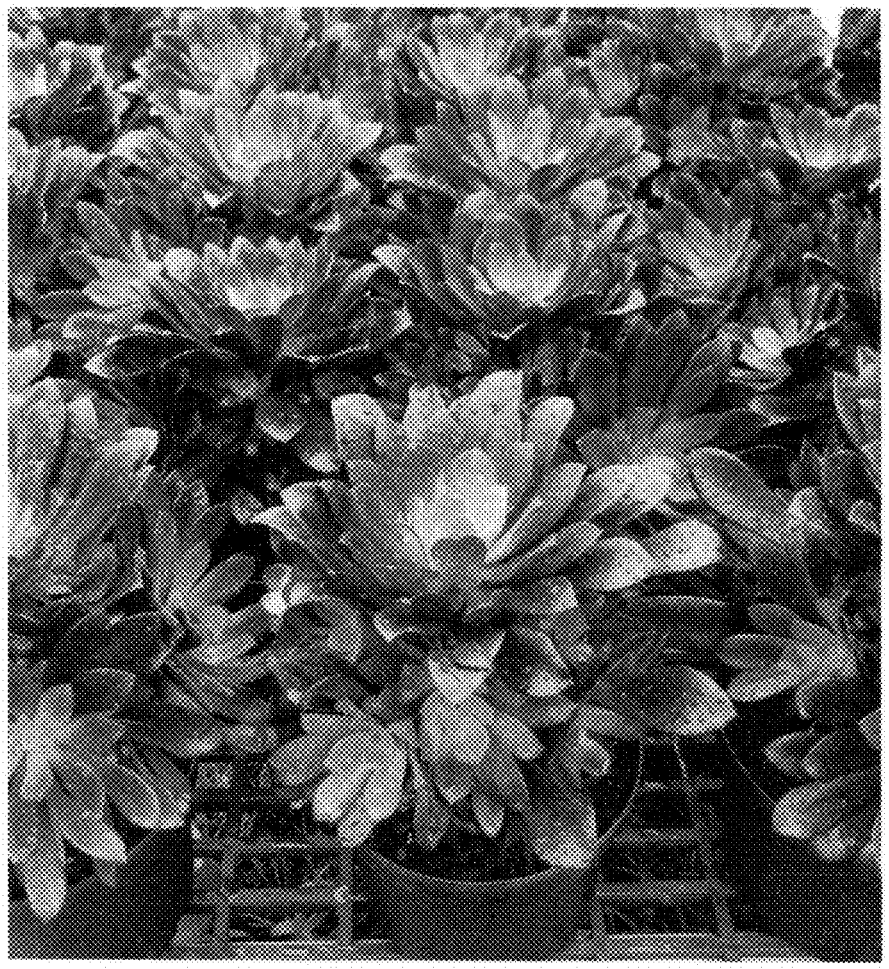

* * * * *